US010610584B2

(12) United States Patent
Dormitzer et al.

(10) Patent No.: US 10,610,584 B2
(45) Date of Patent: Apr. 7, 2020

(54) REVERSE GENETICS SYSTEMS

(71) Applicant: Seqirus UK Limited, Berkshire (GB)

(72) Inventors: Philip Dormitzer, Weston, MA (US); Michael Franti, Blainville (CA); Peter Mason, Somerville, MA (US)

(73) Assignee: Seqirus UK Limited, Berkshire (GB)

( * ) Notice: Subject to any disclaimer, the term of this patent is extended or adjusted under 35 U.S.C. 154(b) by 0 days.

(21) Appl. No.: 15/784,575

(22) Filed: Oct. 16, 2017

(65) Prior Publication Data

US 2018/0236058 A1   Aug. 23, 2018

Related U.S. Application Data

(63) Continuation of application No. 13/388,033, filed as application No. PCT/IB2010/002137 on Jul. 30, 2010, now Pat. No. 9,821,052.

(60) Provisional application No. 61/273,151, filed on Jul. 31, 2009.

(51) Int. Cl.
| | | |
|---|---|---|
| A61K 39/145 | (2006.01) | |
| C07K 14/005 | (2006.01) | |
| C12N 7/00 | (2006.01) | |
| C12N 15/85 | (2006.01) | |
| A61K 39/12 | (2006.01) | |
| A61K 39/00 | (2006.01) | |

(52) U.S. Cl.
CPC ............ *A61K 39/145* (2013.01); *A61K 39/12* (2013.01); *C07K 14/005* (2013.01); *C12N 7/00* (2013.01); *C12N 15/85* (2013.01); *A61K 2039/525* (2013.01); *A61K 2039/5254* (2013.01); *C12N 2760/16122* (2013.01); *C12N 2760/16134* (2013.01); *C12N 2760/16151* (2013.01); *C12N 2760/16222* (2013.01); *C12N 2760/16234* (2013.01); *C12N 2760/16251* (2013.01); *C12N 2800/24* (2013.01); *C12N 2830/00* (2013.01)

(58) Field of Classification Search
None
See application file for complete search history.

(56) References Cited

FOREIGN PATENT DOCUMENTS

| CN | 101302499 A | 11/2008 |
|---|---|---|
| WO | WO 99/50419 | 10/1999 |
| WO | WO 01/90340 A2 | 11/2001 |
| WO | WO 2004/022760 A1 | 3/2004 |
| WO | WO 2007/044024 A2 | 4/2007 |
| WO | WO 2009/000891 A2 | 12/2008 |
| WO | WO 2009/048885 A2 | 4/2009 |
| WO | WO 2010/063804 A1 | 6/2010 |

OTHER PUBLICATIONS de Wit, et al. (2004) "Efficient generation and growth of influenza virus A/PR8/34 from eight cDNA fragments", Virus Research, 103: 155-61.*
Briedis et al., "Influenza B virus genome: sequences and structural organization of RNA segment 8 and the mRNAs coding for the NS1 and NS2 proteins," J Virol, 42(1):186-193, (1982).
Chan et al., "Amplification of the entire genome of influenza a virus H1 N1 and H3N2 subtypes by reverse-transcription polymerase chain reaction," J Virol Methods, 136(1-2):38-43, (2006).
Condreay et al., "Transient and stable gene expression in mammalian cells transduced with a recombinant baculovirus vector," Proc Natl Acad Sci U S A, 96(1):127-132, (1999).
Dortmizer et al., "Synthetic generation of influenza vaccines viruses for rapid responses to pandemics," Sci Transl Med, 5(185):185ra68, (2013).
Gibson et al., "Complete chemical synthesis, assembly, and cloning of a Mycoplasma genitalium genome," Science, 319(5867):1215-1220, (2008).
International Search Report dated Nov. 26, 2010 for PCT Application No. PCT/IB2010/002137, 5 pages.
International Preliminary Report on Patentability dated Jan. 31, 2012 for PCT Application No. PCT/IB2010/002137, 9 pages.
Kitts et al., "Linearization of baculovirus Dna enhances the recovery of recombinant virus expression vectors," Nucleic Acids Res, 18(19):5667-5772, (1990).
Kowalski (2013). "Research Team Publishes New Methods for Synthetic Generation of Influenza Vaccines," Press Release, J. Craig Venter Institute, Retrieved Aug. 11, 2014 from: http://www.jcvi.org/cms/press/press-releases/full-text/article/research-team-publishes-new-methods-for-synthetic-generation-of-influenza-vaccines/.
Lu, "Seamless cloning and gene fusion," Trends Biotechnol, 23(4):199-207, (2005).
PfuTurbo DNA Polymerase Instruction Manual (2011), Catalog #600250, #600252, #600254 and #600256, Revision C, Agilent Technologies, 17 pages.
Smith et al., "Fluorescence detection in automated DNA sequence analysis," Nature, 321(6071):674-679, (1986).
Smith et al., "Generating a synthetic genome by whole genome assembly: phiX174 bacteriophage from synthetic oligonucleotides," Proc Natl Acad Sci U S A, 100(26):15440-15445, (2003).
Stemmer et al., "Single-step assembly of a gene and entire plasmid from large numbers of oligodeoxyribonucleotides," Gene, 164(1):49-53, (1995).
Yount et al., "Systematic assembly of a full-length infectious cDNA of mouse hepatitis virus strain A59," J Virol, 76(21):11065-11078, (2002).
Zhang et al., "A one-plasmid system to generate influenza virus in cultured chicken cells for potential use in influenza vaccine," J Virol, 83(18):9296-9303, (2009).

* cited by examiner

*Primary Examiner* — Robert M Kelly
(74) *Attorney, Agent, or Firm* — Finnegan, Henderson, Farabow, Garrett & Dunner, LLP

(57) ABSTRACT

The invention provides various reverse genetics systems for producing segmented RNA viruses, wherein the systems do not require bacteria for propagation of all of their expression constructs.

21 Claims, No Drawings

Specification includes a Sequence Listing.

SEQUENCE LISTING

```
<160> NUMBER OF SEQ ID NOS: 5

<210> SEQ ID NO 1
<211> LENGTH: 499
<212> TYPE: DNA
<213> ORGANISM: Homo sapiens

<400> SEQUENCE: 1
tttccgagtc cccgtgggga gccggggacc gtcccgcccc cgtccccgg  gtgccgggga      60 gcggtccccg ggccgggccg cggtccctct gccgcgatcc tttctggcga gtccccgtgc     120
ggagtcggag agcgctccct gagcgcgcgt gcggcccgag aggtcgcgcc tggccggcct     180
tcggtccctc gtgtgtcccg gtcgtaggag gggccggccg aaaatgcttc cggctcccgc     240
tctggagaca cgggccggcc ccctgcgtgt ggcacgggcg gccgggaggg cgtccccggc     300
ccggcgctgc tcccgcgtgt gtcctggggt tgaccagagg gccccgggcg ctccgtgtgt     360
ggctgcgatg gtggcgtttt tggggacagg tgtccgtgtc gcgcgtcgcc tgggccggcg     420
gcgtggtcgg tgacgcgacc tcccggcccc gggggaggta tatctttcgc tccgagtcgg     480
cattttgggc cgcccgggt                                                  499

<210> SEQ ID NO 2
<211> LENGTH: 219
<212> TYPE: DNA
<213> ORGANISM: Homo sapiens

<400> SEQUENCE: 2
gccgggaggg cgtccccggc ccggcgctgc tcccgcgtgt gtcctggggt tgaccagagg      60
gccccgggcg ctccgtgtgt ggctgcgatg gtggcgtttt tggggacagg tgtccgtgtc     120
gcgcgtcgcc tgggccggcg gcgtggtcgg tgacgcgacc tcccggcccc gggggaggta     180
tatctttcgc tccgagtcgg cattttgggc cgcccgggt                            219
```

<210> SEQ ID NO 3
<211> LENGTH: 1814
<212> TYPE: DNA
<213> ORGANISM: Canis spec.
<220> FEATURE:
<221> NAME/KEY: misc_feature
<222> LOCATION: 1647
<223> OTHER INFORMATION: n = a, t, c or g

<400> SEQUENCE: 3

```
agcgtgagca ggagaattct ggagaaacag attgtgttat aagaaagaaa gaaagaaaga      60
aagaaagaaa gaaagagaaa atccttatgt tctttgagcc tcccctcccc cccagaattg     120
agttcctctt ccacgacctc ttctcattca acccaataga caagtatttg ggggggggg     180
gtcaggtccc agacgcttaa agggtggaag tgaaagtggt gcggggaag ggggggggca     240
caccgtcctc tccagcgcct ttggttcaaa cctccttcgt gacctccctc cctccctccc     300
tccttcgtct tataaatata taaataaaat cctaagaaaa agaaaaaaa aaaaaaaaaa     360
aaaggaagga cacgagaaaa aacggtgcat ccgttgccgt cctaagagtc ctcgcctggt     420
ttcggctcta cgttccctcc ctgacctcgg aaacgtgcct gagtcgtccc gggagccccg     480
cgcggcgagc gcgacccct ttccgggcgg cagcgggccc ggacggacgg acggacggac     540
ggacgggttt tccaaggctc ccccgccccg ggaggacggg ggttcgcgcg gtgcgcggcc     600
gtgtgctccc ggggccctcc gccgtccccg ggccgagagg cgagatccga ggcgccctga     660
cggcctcgcc gcccggatct gtcccgctgt cgttcgcgcc ggttgtcggg tgccacctgg     720
cggccgcttt tatagagcgt gtcccctccg gaggctcggc ggcgacaggc aaggaacagc     780
tttggtgtcg gtttcccggg gccgagttcc aggaggaggg cggctccggc gcgagcgtcc     840
ggctgtcgcc ggggcctcgg cgcgcgatgc gctcgccgga gattggacct ccggagctgc     900
gagggagtgt cgccgtcgcc gctgtcgccg ctgtcgcctc cgcctcgctc ccggaggagg     960
ccgtgcgggc cgcctgggtg ggtcgaccag cacccgccgg tggctcctcc tccgcccgcg    1020
cggaccgacc tgggccgcct cggggggcggg ggacagggtg tgtcccgccg tccgtcctgt    1080
ggctccgggc gatcttcggg ccttccttcc gtgtcactcg gttgtctccc gtggtcacgc    1140
cctggcgacg gggaccggtc tgagcctgga ggggaagccc gtgggtggcg cgacagaccc    1200
ggctgcgggc acgtgtgggg gtcccggggcg tcggacgcga ttttctcccc ttgttccgag    1260
gcccgctgcg gaggtgggtc ccgggcggtc ggaccgggtg ccacgcgggg gtgggcgggc    1320
cgtccgttcg ggcgtccggc cccggtggcg attcccggtg aggctgcctc tgccgcgcgt    1380
ggccctccac ctcccctggc ccgagccggg gttggggacg gcggtaggca cggggcggtc    1440
ctgagggccg cggggggacgg cctccgcacg gtgcctgcct ccggagaact tgatgatttt    1500
ttcaaagtct cctcccggag atcactggcg tggcggcgtg gcggcgtggc ggcgtggcgg    1560
cgtggcgtct ccaccgaccg cgtatcgccc ctcctcaccc ccccccccc ccgggttacc    1620
tggggcgacc agaaagccct ggggcgcggg ggctccgtgg ggtgggggtg ggggggcgcc    1680
gtggggcagg ttttgggtac agttggccgt gtcacggtcc cgggaggtcg cggtgacctg    1740
tggctggtcc ccgccggcag gcgcggttat tttcttgccc gaaatgaaca tttttttgttg    1800
ccaggtaggt gctg                                                     1814
```

<210> SEQ ID NO 4
<211> LENGTH: 474
<212> TYPE: DNA
<213> ORGANISM: Canis spec.
<220> FEATURE:

```
<221> NAME/KEY: misc_feature
<222> LOCATION: 307
<223> OTHER INFORMATION: n = a, t, c or g

<400> SEQUENCE: 4
cccggtggcg attcccggtg aggctgcctc tgccgcgcgt ggccctccac ctcccctggc      60
ccgagccggg gttggggacg gcggtaggca cggggcggtc ctgagggccg cggggggacgg    120 cctccgcacg gtgcctgcct ccggagaact ttgatgattt ttcaaagtct cctcccggag    180
atcactggcg tggcggcgtg gcggcgtggc ggcgtggcgg cgtggcgtct ccaccgaccg    240
cgtatcgccc ctcctcaccc cccccccccc ccgggttacc tggggcgacc agaaagccct    300
gggggcnggg ggctccgtgg ggtggggggtg gggggcgcc gtggggcagg ttttgggtac    360
agttggccgt gtcacggtcc cgggaggtcg cggtgacctg tggctggtcc ccgccggcag    420
gcgcggttat tttcttgccc gaaatgaaca tttttgttg ccaggtaggt gctg           474

<210> SEQ ID NO 5
<211> LENGTH: 288
<212> TYPE: DNA
<213> ORGANISM: Canis spec.
<220> FEATURE:
<221> NAME/KEY: misc_feature
<222> LOCATION: 121
<223> OTHER INFORMATION: n = a, t, c or g

<400> SEQUENCE: 5
ggcgtggcgg cgtggcggcg tggcggcgtg gcggcgtggc gtctccaccg accgcgtatc     60
gcccctcctc accccccccc ccccccgggt tacctggggc gaccagaaag ccctgggggc    120 nggggggctcc gtggggtggg ggtgggggggg cgccgtgggg caggtttgg gtacagttgg   180 ccgtgtcacg gtcccgggag gtcgcggtga cctgtggctg gtccccgccg gcaggcgcgg    240
ttattttctt gcccgaaatg aacatttttt gttgccaggt aggtgctg                288
```

REVERSE GENETICS SYSTEMS

This application is a continuation of U.S. application Ser. No. 13/388,033, filed May 11, 2012, now U.S. Pat. No. 9,821,052, which is a national stage of International Application No. PCT/IB2010/002137, filed Jul. 30, 2010, which claims priority from U.S. provisional patent application 61/273,151, filed 31 Jul. 2009, the complete contents of each of which are incorporated herein by reference.

TECHNICAL FIELD

This invention is in the field of reverse genetics. Furthermore, it relates to preparing viruses e.g. for use in manufacturing vaccines for protecting against various viruses.

BACKGROUND ART

Reverse genetics permits the recombinant expression and manipulation of viruses in cell culture. It is a powerful tool in virology and vaccine manufacture because it allows rapid production and/or mutation of viruses, including reassortant production. The method involves transfecting host cells with one or more plasmids which encode the viral genome then isolating (or "rescuing") virus from the cells. It can be used for the production of a wide variety of RNA viruses, including positive-strand RNA viruses [1,2], negative-strand RNA viruses [3,4] and double-stranded RNA viruses [5].

A drawback of known methods is that they rely on plasmids: Generating these plasmids requires cloning steps to be performed in bacteria, which can take several days or weeks to perform and verify for a segmented RNA virus. Such delays interfere with the timetable for yearly production of seasonal influenza vaccines and also prevent a rapid response to a pandemic outbreak. Furthermore, the use of bacteria entails the risk that bacterial contaminants might be introduced when the plasmids are used to transfect a host cell for virus production. These drawbacks are addressed in reference 6 by using linear expression constructs instead of plasmids. The linear expression constructs do not contain amplification and/or selection sequences which are used during bacterial propagation and almost always results in the molecular cloning of a single representative of a viral quasispecies. Such linear expression constructs can be used to transfect host cells directly, giving a much more rapid reverse genetics system: reference 6 suggests that transfection of the linear constructs can be achieved within hours of receiving a viral isolate, avoiding the time required for molecular cloning and allowing access to useful members of the original viral quasispecies population.

DISCLOSURE OF THE INVENTION

For a segmented virus the method used in reference 6 uses one linear construct per viral segment. Thus reverse genetics virus production by this method requires transfection of a host cell with eight different constructs. An object of the invention is to avoid the need for such multiple transfections. More generally, it is an object of the invention to provide further and improved methods for practising reverse genetics for segmented RNA viruses, and in particular to provide further methods which do not require the use of bacteria. The invention provides various reverse genetics systems for producing segmented RNA viruses, wherein the systems do not require bacteria for propagation of all of their expression constructs. Ideally, bacteria are not required at all.

In a first aspect, a reverse genetics system is based on a non-bacterial expression construct which encodes at least two viral genome segments. This system reduces the number of constructs which have to be transfected into a host cell for production of a complete viral genome. For instance, a single construct can be used to encode eight influenza virus segments, thereby giving an 8-fold reduction in the complexity of transfections as compared to reference 6. Thus the invention provides a non-bacterial expression construct comprising coding sequences for expressing at least two different genome segments of a segmented RNA virus. The invention also provides a eukaryotic host cell including this non-bacterial expression construct. The invention also provides a set of two or more such non-bacterial expression constructs, wherein the set encodes a complete segmented RNA virus genome.

In a second aspect, a reverse genetics system is based on a combination of (i) at least one bacterial expression construct and (ii) at least one non-bacterial expression construct. Each of these two types of constructs provides at least one viral genome segment. Although this aspect does not totally avoid the use of bacteria for preparing the system, it is still powerful. For instance, constructs expressing a subset of the viral segments can be propagated and manipulated in bacteria, taking advantage of the wide range of convenient molecular biological techniques which are available. The segments of this subset can be those which do not often need to be changed from strain to strain. The remaining viral segments can be encoded by non-bacterial expression constructs, and these constructs can be rapidly prepared at short notice without requiring bacterial work. This combination thus means that efforts can focus on the segments of interest at short notice, and the constructs can be combined with an existing set of "background" segments which were already available. Thus the invention provides a set of expression constructs comprising (i) at least one plasmid comprising coding sequence(s) for one or more genome segments of a segmented RNA virus and (ii) at least one non-bacterial expression construct comprising coding sequence(s) for one or more genome segments of the RNA virus, wherein the combination of bacterial and non-bacterial constructs provides at least two different genome segments of the RNA virus. The invention also provides a eukaryotic host cell including this set of constructs.

In a third aspect, the invention provides a host cell including a linear expression construct which comprises coding sequences for at least two different genome segments of a segmented RNA virus. This cell may be bacterial but is preferably eukaryotic.

In a fourth aspect, the invention provides a bacterial plasmid comprising coding sequences for eight different genome segments of an influenza virus, wherein expression of each segment is controlled by either (i) a mammalian pol-I promoter or (ii) a bacteriophage polymerase promoter. The invention also provides a cell including this construct, and this cell may be bacterial or eukaryotic.

The invention further provides a process for preparing a host cell of the invention, comprising a step of inserting into the cell one or more expression construct(s) mentioned above.

The invention further provides a process for RNA expression in a eukaryotic host cell of the invention, comprising a step of culturing the host cell under conditions such that expression of the RNA virus segments occurs from the expression constructs.

The invention further provides a method for producing a segmented RNA virus, comprising a step of culturing a host cell of the invention under conditions such that expression of the RNA virus segments occurs from the expression constructs to produce the virus. Virus produced in this way may then be purified from the host cells or from a culture of the host cells. The invention also provides virus obtained by this process. This virus may be used to infect eggs or cells to grow virus for vaccine manufacture. Thus the invention provides a method for preparing a viral vaccine, comprising a step of infecting a culture host (e.g. eggs or cells) with a virus of the invention, growing the virus, and then preparing vaccine from the grown virus.

The invention also provides a process for preparing a DNA molecule which comprises coding sequences for expressing at least two different segments of a segmented RNA virus genome (e.g. a non-bacterial expression construct of the invention), wherein the DNA is prepared at least in part by chemical synthesis.

The invention also provides a process for preparing a DNA molecule which comprises coding sequences for expressing at least two different segments of a segmented RNA virus genome (e.g. a non-bacterial expression construct of the invention), wherein the process comprises steps of: (i) synthesising a plurality of overlapping fragments of the DNA molecule, wherein the overlapping fragments span the complete DNA molecule; and (ii) joining the fragments to provide the DNA molecule. The DNA molecule may then be recovered and used in the reverse genetics methods of the invention e.g. it can be inserted into a eukaryotic cell for generation of the segmented RNA virus. Preferably the DNA molecule is not inserted into a bacterial cell between its recovery and its insertion into the eukaryotic cell i.e. the construct is used directly for viral rescue without any intermediate bacterial amplification.

The invention also provides a library of expression constructs for a segmented RNA virus, wherein each expression construct comprises a coding sequence for at least one genome segment of the virus. The library includes at least one construct for each segment of the genome, such that the whole genome can be represented by selecting a subset of the library. Some viral segments may be represented more frequently than others e.g. an influenza virus library may include many more HA and NA segments than the average. To construct a desired viral genome of interest, library members encoding each desired segment are selected and then expressed to give the desired virus. The library is particularly powerful for influenza virus by permitting rapid reassortment of backbone genome segments with HA and NA segments of interest to produce a useful virus for vaccine production.

Non-Bacterial Expression Constructs

The first, second and third aspects of the invention utilise one or more "non-bacterial expression constructs". This term means that the construct can drive expression in a eukaryotic cell of viral RNA segments encoded therein, but it does not include components which would be required for propagation of the construct in bacteria. Thus the construct will not include a bacterial origin of replication (ori), and usually will not include a bacterial selection marker (e.g. an antibiotic resistance marker). These components are not required for driving the desired viral RNA expression in a eukaryotic host cell and so are superfluous when bacteria are not used for propagation of the constructs. Absence of these propagation components means that the constructs will not be replicated if they are introduced into bacteria.

The non-bacterial construct may be linear or circular. Linear constructs are more usual (as seen in reference 6), but circular constructs can also be used. Circular constructs can be made by circularising linear constructs and vice versa. Methods for such circularisation are described in ref. 6. Linearisation of a circular construct can be achieved in various easy ways e.g. utilising one or more restriction enzyme(s), or by amplification from a template (including a circular template) using a nucleic acid amplification technique (e.g. by PCR).

A non-bacterial construct includes coding sequence(s) for one or more viral RNA segment(s). Constructs for the first and third aspects encode at least two different viral RNA segments. The encoded segments can be expressed and then function as viral RNAs which can be packaged into virions to give recombinantly expressed virus. Thus the constructs are suitable for producing a RNA virus by reverse genetics, either alone or in combination with other constructs.

The construct will usually be made of double-stranded DNA. Such constructs can conveniently be made by known methods of DNA synthesis and assembly. Modern techniques can provide synthetic DNA molecules encoding a complete virus even if it has many genomic segments. For example, a construct expressing all eight segments of the influenza virus genome requires about 25,000 base pairs (25 kbp) of DNA, which is well within the capability of current construct synthesis e.g. reference 7 reports chemical synthesis of a 32 kbp gene by assembly of individual ~5 kbp synthetic fragments, and reference 8 reports the production of a 583 kbp synthetic chromosome via intermediate stages of about 5 kbp, 7 kbp, 24 kbp, 72 kbp or 144 kbp long. See below for further details.

Such synthetic methods are the preferred way of providing constructs (and in particular of providing linear constructs). Instead of using chemical synthesis, however, DNA for a construct can be prepared from a RNA virus by reverse transcription to provide a cDNA, and extra DNA sequences can then be joined to the cDNA (e.g. by ligation) or the cDNA can be incorporated into a larger DNA construct. In some embodiments, a mixture of enzymatic and chemical methods is used e.g. reverse transcription followed by chemical addition to the termini.

As well as being free from any bacterial propagation elements, the non-bacterial construct may also be free from any bacterial DNA modifications. Thus the construct may include no methylated adenine residues, and any methylated cytosine residues will be in the context of a CpG dinucleotide motif i.e. there will be no methylated cytosines which are not followed by a guanidine.

The construct can be introduced into a host cell by any suitable transfection method e.g. by electroporation, lipofection, DEAE-dextran, calcium phosphate precipitation, liposomes, gene guns, microparticle bombardment or microinjection. Once transfected, the host cell will recognise genetic elements in the construct and will begin to express the encoded viral RNA segments.

Construct Synthesis

As mentioned above, a DNA expression construct may be prepared by chemical synthesis at least in part. The construct comprises coding sequences for expressing at least two different segments of a segmented RNA virus genome (and preferably for expressing the complete genome of a segmented RNA virus) and can conveniently be prepared using the synthetic methods disclosed in reference 8.

The synthetic method may involve notionally splitting the desired DNA sequence into fragments. These fragments may again be notionally split one or more times, eventually arriving at a set of fragments which are each of a size which can be prepared by a chosen DNA synthesis method e.g. by phosphoramidite chemistry. These fragments are then synthesised and joined to give the longer fragments from the notional splitting stage, and these longer fragments are then joined, etc. until the complete sequence is eventually prepared. In this way reference 8 prepared a 583 kbp genome by assembling ~$10^4$ 50 mer oligonucleotides in various stages. The 50 mers were assembled into cassettes 5-7 kb long, and these cassettes were then assembled into ~24 kbp fragments, which were then assembled into ~72 kbp fragments, then ~144 kbp, then giving two ~290 kbp constructs, which were finally joined to give the complete genome.

The fragments are designed to overlap, thereby permitting them to assemble in the correct order. For instance, the cassettes overlapped by at least 80 bp, thereby enabling their assembly into the ~24 kbp fragments, etc. Thus the method involves the synthesis of a plurality of overlapping fragments of the desired DNA molecule, such that the overlapping fragments span the complete DNA molecule. Both ends of each fragment overlap with a neighbouring 5' or 3' fragment, except for the terminal fragments of a linear molecule where no overlap is required (but to synthesise a circular molecule, the two terminal fragments should overlap). Fragments at each stage may be maintained as inserts in vectors e.g. in plasmids or BAC or YAC vectors. Assembly of fragments during the synthetic process can involve in vitro and/or in vivo recombination. For in vitro methods, digestion with a 3' exonuclease can be used to expose overhangs at the terminus of a fragment, and complementary overhangs in overlapping fragments can then be annealed, followed by joint repair ("chewback assembly"). For in vivo methods, overlapping clones can be assembled using e.g. the TAR cloning method disclosed in reference 8. For fragments <100 kbp (e.g. easily enough to encode all segments of an influenza virus genome) it is readily possible to rely solely on in vitro recombination methods.

Other synthetic methods may be used. For instance, reference 7 discloses a method in which fragments ~5 kbp are synthesised and then assembled into longer sequences by conventional cloning methods. Unpurified 40 base synthetic oligonucleotides are built into 500-800-bp synthons by automated PCR-based gene synthesis, and these synthons joined into multisynthon ~5 kbp segments using a small number of endonucleases and "ligation by selection." These large segments can be subsequently assembled into longer sequences by conventional cloning. This method can readily provide a 32 kbp DNA molecule, which is easily enough to encode a complete influenza virus.

Similarly, reference 9 discloses a method where a 32 kb molecule was assembled from seven DNA fragments which spanned the complete sequence. The ends of the seven DNAs were engineered with unique junctions, thereby permitting assembly only of adjacent fragments. The interconnecting restriction site junctions at the ends of each DNA are systematically removed assembly.

Once the complete DNA molecule has been assembled, it is purified and may be inserted directly into eukaryotic cells for virus production, without involving an intermediate step where the DNA is present inside a bacterium.

When prepared by these methods, a DNA expression construct of the invention may include one or more "watermark" sequences. These are sequences which can be used to identify or encode information in the DNA. It can be in either noncoding or coding sequences. Most commonly, it encodes information within coding sequences without altering the amino acid sequences. For DNAs encoding segmented RNA viral genomes, any watermark sequences are ideally included in intergenic sites because synonymous codon changes may have substantial biological effects for encoded RNA segments.

Plasmids

The second and fourth aspects of the invention involve the use of plasmids. These plasmids can conveniently be propagated in bacteria and so include a bacterial origin of replication (ori) and usually also include a bacterial selection marker (e.g. an antibiotic resistance marker). Thus the plasmids are readily distinguished (both by sequence and by function) from the non-bacterial expression constructs discussed above. In general terms, the plasmids may be the same as plasmids already known in the art for reverse genetics, but the prior art does not disclose their use in combination with non-bacterial expression constructs for virus rescue.

The plasmid also includes the necessary genetic elements to survive in a eukaryotic host cell, in which virus production can occur. Thus the plasmid is a shuttle plasmid which can be propagated, manipulated and/or amplified in a bacterial host but which can drive viral RNA expression in a eukaryotic host.

The plasmid encodes at least one viral RNA segment (eight influenza virus segments in the fourth aspect) and in a eukaryotic host cell these coding sequences can be expressed and then function as viral RNAs which can be packaged into virions to give recombinantly expressed virus.

The plasmid can be introduced into a eukaryotic host cell by any suitable transfection method e.g. by electroporation, lipofection, gene guns, or microinjection. Once transfected, the host cell will recognise genetic elements in the construct and will begin to express the encoded viral RNA segment(s).

When a plasmid encodes multiple RNA segments, steps can be taken to minimise intraplasmid recombination. The presence of multiple identical promoters and terminators (both pol-I and pol-II) can increase this risk, as can the use of a ori which provides a high copy number during bacterial propagation. Thus a plasmid may advantageously have a relatively low copy number when present in bacteria e.g. <50 copies per *E. coli* cell. Various low copy number vectors are available e.g. the vectors used in reference 10, vectors which include the p15a ori or a plasmid F ori [11], etc. It is also useful to use promoters having different sequences and/or to avoid including superfluous coding regions which provide extra promoters. Steps such as these can improve the stability of a plasmid.

Expression Constructs

Non-bacterial and plasmid expression constructs used with the invention encode viral RNA segment(s). These coding sequences can be expressed in a suitable eukaryotic host cell to provide viral RNAs which can be packaged into virions to give recombinantly expressed virus.

Expression of a viral RNA segment will be controlled by a promoter upstream of the RNA-encoding sequence. The promoter for expressing a viral RNA segment in an animal cell will be recognised by a DNA-dependent RNA polymerase and will usually be a pol-I promoter (see below). Other systems are available, however, and it is known to use bacteriophage or bacterial RNA polymerase promoters, such as the T7 RNA polymerase, in association with an in situ source of the polymerase [12]. Each viral segment has its own promoter, and these may be the same or different as each other.

Where the virus is a positive-strand RNA virus it is often sufficient to transfect a cell with an expression construct encoding only the viral segments. For example, the transfection of plasmids encoding the poliovirus genome resulted in the recovery of infectious poliovirus [1,2]. Reverse genetics for negative-strand RNA viruses presents extra challenges because the antisense viral RNA is usually non-infective and thus requires viral proteins to complete the life cycle. Thus viral proteins such as the viral polymerase are supplied to the cell, either delivered as protein or as a gene for in situ protein expression.

Thus an expression construct may include coding sequences for expressing viral proteins in eukaryotic cells, particularly for negative-strand viruses. Suitable promoters for protein expression include those from cytomegalovirus (CMV). Co-expression of the viral segments and viral proteins gives all of the necessary elements in situ for recombinant assembly of a virus in the host cell. It is useful to include the protein-coding sequences on the same construct as the RNA-coding sequences, but it is also possible to use different constructs for RNA and protein expression. Where the protein-coding and RNA-coding sequences are in the same construct, they may be different sequences but it is instead possible to drive expression from two different promoters to provide both RNA and protein expression from the same DNA sequence.

Bi-directional constructs are known in the art for expressing viral RNA from a pol-I promoter and viral protein from a pol-II promoter attached to the same DNA sequence (e.g. see reference 13). The two promoters drive expression in different directions (i.e. both 5' to 3' and 3' to 5') from the same construct and can be on different strands of the same double stranded DNA. The use of a common DNA sequence reduces the total number and/or length of expression constructs required by the host cell. A bi-directional expression construct can include a gene or cDNA located between an upstream pol-II promoter and a downstream pol-I promoter. Transcription of the gene or cDNA from the pol-II promoter produces capped positive-sense viral mRNA which can be translated into a viral protein, while transcription from the pol-I promoter produces uncapped negative-sense vRNA.

An expression construct will typically include a RNA transcription termination sequence for each transcription unit. The termination sequence may be an endogenous termination sequence or a termination sequence which is not endogenous to the host cell. Suitable termination sequences will be evident to those of skill in the art and include, but are not limited to, RNA polymerase I transcription termination sequences, RNA polymerase II transcription termination sequences, and ribozymes. Furthermore, the expression constructs may contain one or more polyadenylation signals for mRNAs, particularly at the end of a gene used for protein expression. The coding sequences for viral RNA segments are typically flanked by a pol-I promoter at one end and a pol-II promoter at the other end, with pol-I promoter and terminator sequences flanking the segment-encoding sequence, flanked in turn by pol-II promoter and terminator sequences. The spacing of these various sequence elements with reference to each other is important for the polymerase to correctly initiate and terminate replication, but this is not difficult to achieve.

An expression construct may include a selectable marker for selection in eukaryotic cells.

An expression construct may include one or more multiple cloning sites to facilitate introduction of a DNA sequence.

Where separate coding sequences are used for viral RNAs and proteins, it is possible to use different sequences e.g. the protein-coding sequence could be codon-optimised for a particular host cell, whereas the RNA-coding sequence uses the codons natural to the virus in question. Codon optimisation of a RNA-coding sequence is less useful because the RNA should be optimal for virion packaging rather than for recombinant protein expression.

Where the expression host is a canine cell, such as a MDCK cell line, protein-coding regions may be optimised for canine expression e.g. using a pol-II promoter from a wild-type canine gene or from a canine virus, and/or having codon usage more suitable for canine cells than for human cells. For instance, whereas human genes slightly favour UUC as the codon for Phe (54%), in canine cells the preference is stronger (59%). Similarly, whereas there is no majority preference for Ile codons in human cells, 53% of canine codons use AUC for Ile. Canine viruses, such as canine parvovirus (a ssDNA virus) can also provide guidance for codon optimisation e.g. 95% of Phe codons in canine parvovirus sequences are UUU (vs. 41% in the canine genome), 68% of Ile codons are AUU (vs. 32%), 46% of Val codons are GUU (vs. 14%), 72% of Pro codons are CCA (vs. 25%), 87% of Tyr codons are UAU (vs. 40%), 87% of His codons are CAU (vs. 39%), 92% of Gln codons are CAA (vs. 25%), 81% of Glu codons are GAA (vs. 40%), 94% of Cys codons are UGU (vs. 42%), only 1% of Ser codons are UCU (vs. 24%), CCC is never used for Phe and UAG is never used as a stop codon. Thus protein-coding genes can be made more like genes which nature has already optimised for expression in canine cells, thereby facilitating expression.

RNA Polymerase I Promoters

Most reverse genetics methods use expression vectors which comprise a RNA polymerase I (RNA pol-I) promoter to drive transcription of viral RNA segments. The pol-I promoter gives a transcript with unmodified 5' and 3' ends which is necessary for full infectivity of many viruses e.g. influenza.

Natural pol-I promoters are bipartite, having two separate regions: the core promoter and the upstream promoter element (UPE). Although this general organisation is common to pol-I promoters from most species, however, the actual sequences of the promoters vary widely. The core promoter surrounds the transcription startpoint, extending from about −45 to +20, and is sufficient to initiate transcription. The core promoter is generally GC rich. Although the core promoter alone is sufficient to initiate transcription, the promoter's efficiency is very much increased by the UPE. The UPE typically extends from about −180 to −107 and is also GC rich. The activity of the promoter may be further enhanced by the presence of distal enhancer-like sequences, which might function by stabilizing the pre-initiation complex.

The sequences of pol-I promoters have been identified in a variety of species, including human, dog and chicken. The invention will typically use a pol-I promoter which is endogenous to the host cell, as the activity of pol-I promoters can be restricted to a narrow host range. In some circumstances, however, a pol-I promoter can be active outside its natural host e.g. human pol-I promoters can be active in monkey cells, and also in some dog cells.

Expression constructs can include at least one core promoter; preferably they also include at least one UPE, and they may also include one or more enhancer elements. It is also possible to use the fragments of natural promoters, provided that these fragments can initiate transcription. A human pol-I promoter which can be used according to the invention may comprise the sequence of SEQ ID NO: 1 or SEQ ID NO: 2, or a variant thereof. Where a canine promoter is used according to the invention, it may comprise the sequence of SEQ ID NO: 3, SEQ ID NO: 4 or SEQ ID NO: 5, or a variant thereof. Canine pol-I promoters for reverse genetics are disclosed in references 14 & 15.

The pol-I promoter may comprise (i) a sequence having at least p % sequence identity to any of SEQ ID NOs: 1 to 5, and/or (ii) a fragment any of SEQ ID NOs: 1 to 5, provided that the promoter has the ability to initiate and drive transcription of an operatively linked RNA-encoding sequence in a host cell of interest. The value of p may be 75, 80, 85, 90, 95, 96, 97, 98, 99 or more. The fragment may itself be of sufficient length to drive expression (e.g. SEQ ID NO: 4 is a fragment of SEQ ID NO: 3) or the fragment may be joined to other sequences and this combination will drive expression. The ability of such pol-I promoters to drive expression in a host cell of interest can readily be assessed e.g. using the assays described above with an antisense reporter gene under control of the promoter.

Virus Preparation

The invention is useful for the production of virus strains, including modified or reassortant strains. The technique can use in vitro manipulation of DNA constructs to generate combinations of viral segments, to facilitate manipulation of coding or non-coding sequences in the viral segments, to introduce mutations, etc. The production of reassortant virus strains is useful as it can significantly decrease the time needed to obtain a reassortant seed virus which is particularly beneficial in situations where a rapid production of vaccine is needed to counteract an epidemic. Thus, it is preferred that expression constructs are used to express viral segments from or derived from at least two different wild-type strains.

In order to produce a recombinant virus, a cell must express all segments of the viral genome which are necessary to assemble a virion. DNA cloned into the expression constructs of the invention preferably provides all of the viral RNA and proteins, but it is also possible to use a helper virus to provide some of the RNA and proteins, although systems which do not use a helper virus are preferred.

To provide all viral segments from the constructs of the invention, various arrangements are possible. According to the first aspect, all viral segments can be encoded on non-bacterial expression constructs, provided that at least one of these constructs encodes at least two viral genome segments (unlike reference 6); and ideally, all viral genome segments are encoded on a single non-bacterial construct, such that transfection with that single construct is enough to provide a host cell with the ability to produce the virus of interest. In contrast, according to the second aspect the viral segments are split between bacterial and non-bacterial expression constructs, and their combined presence in a cell provides expression of all viral segments.

It can be advantageous to split the viral segments between more than one expression construct, even with the first aspect. Taking vaccine production strains of influenza A virus as an example, six of the eight segments typically do not change from year to year, and every season this constant viral backbone is supplemented by seasonal HA and NA segments. In this situation it can be helpful to encode the six backbone segments on one construct, and to encode the two other variable segments either together on a second construct or separately on a second and third construct. This permits the seasonal variations to be performed on a smaller construct, and also allows the backbone construct to be optimised specifically for backbone expression.

Viruses

The methods of the invention may be practised with any segmented RNA virus. Such viruses can be positive-stranded, negative-stranded, or double-stranded.

Where the virus is a negative-strand RNA virus, the virus may be from a family selected from the group consisting of Paramyxoviridae, Pneumovirinae, Rhabdoviridae, Filoviridae, Bornaviridae, Orthomyxoviridae, Bunyaviridae, or Arenaviridae. Furthermore, the virus may be a virus from a genus selected from the group consisting of Paramyxovirus, Orthomyxovirus, Respirovirus, Morbillivirus, Rubulavirus, Henipaviras, Avulavirus, Pneumovirus, Metapneumovirus, Vesiculovirus, Lyssavirus, Ephemerovirus, Cytorhabdovirus, Nucleorhabdovirus, Novirhabdovirus, Marburgvirus, Ebolavirus, Bomavirus, Influenzavirus A, Influenzavirus B, Influenzavirus C, Thogotovirus, Isavirus, Orthobunyavirus, Hantavirus, Nairovirus, Phlebovirus, Tospovirus, Arenavirus, Ophiovirus, Tenuivirus, or Deltavirus. In specific embodiments, the negative-strand RNA virus is selected from the group consisting of Sendai virus, Measles virus, Mumps virus, Hendra virus, Newcastle disease virus, Human respiratory syncytial virus, Avian pneumovirus, Vesicular stomatitis Indiana virus, Rabies virus, Bovine ephemeral fever virus, Lettuce necrotic yellows virus, Potato yellow dwarf virus, Infectious hematopoietic necrosis virus, Lake Victoria marburgvirus, Zaire ebolavirus, Boma disease virus, Influenza virus, Thogoto virus, Infectious salmon anemia virus, Bunyamwera virus, Hantaan virus, Dugbe virus, Rift Valley fever virus, Tomato spotted wilt virus, Lymphocytic choriomeningitis virus, Citrus psorosis virus, Rice stripe virus, and Hepatitis delta virus. In preferred embodiments, the virus is an influenza virus (see below).

Where the virus is a positive-strand RNA virus, the virus may be from a family selected from the group consisting of Arteriviridae, Coronaviridae, Picornaviridae and Roniviridae. Furthermore, the virus may be a virus from a genus selected from the group consisting of Arterivirius, Coronavirus, Enterovirus, Torovirus, Okavirus, Rhinovirus, Hepatovirus, Cardiovirus, Aphthovirus, Parechovirus, Erbovirus, Kobuvirus and Teschovirus. In specific embodiments, the virus is selected from the group consisting of severe acute respiratory syndrome (SARS) virus, polio virus, Human enterovirus A (HEV-A), Human enterovirus B (HEV-B), Human enterovirus C, Human enterovirus D, Hepatitis A and Human rhinovirus A and B.

Where the virus is a double-stranded RNA virus, the virus may be from a family selected from the group consisting of Birnaviridae, Cystoviridae, Hypoviridae, Partitiviridae, Reoviridae and Totiviridae. Furthermore, the virus may be a virus from a genus selected from the group consisting of Aquabirnavirus, Avibimavirus, Entomobirnavirus, Cystovirus, Partitivirus, Alphacryptovirus, Betacryptovirus, Aquareovirus, Coltivirus, Cypovirus, Fijivirus, Idnoreovirus, Mycoreovirus, Orbivirus, Orthoreovirus, Oryzavirus, Phytoreovirus, Rotavirus and Seadornavirus.

The present invention is particularly suitable for viruses which undergo rapid mutation and where the recombinant approach allows for a more rapid isolation of the virus which can then be further propagated to obtain suitable vaccines. Therefore, in a preferred embodiment the virus is influenza.

Influenza Viruses

The invention is particularly suitable for use with influenza A virus and influenza B virus, for which reverse genetics has been well characterized. Influenza viruses are segmented negative strand RNA viruses. Influenza A and B viruses have eight segments (PB2, PB1, PA, HA, NP, NA, M and NS), whereas influenza C virus has seven (no NA segment). The virus usually requires the presence of at least four viral proteins (PB1, PB2, PA and nucleoprotein) to initiate replication. At least these four viral proteins should thus be provided by protein-encoding expression constructs.

Preferred expression systems for influenza A viruses encode genome segments derived from a plurality of different wild-type strains. The system may encode 1 or more (e.g. 1, 2, 3, 4, 5 or 6) genome segments from a PR/8/34 strain (A/Puerto Rico/8/34), but usually this/these will not include the PR/8/34 HA segment and usually will not include the PR/8/34 NA segment. Thus the system may encode at least one of segments NP, M, NS, PA, PB1 and/or PB2 (possibly all six) from PR/8/34.

Other useful expression systems for influenza A viruses may encode 1 or more (e.g. 1, 2, 3, 4, 5 or 6) genome segments from an AA/6/60 influenza virus (A/Ann Arbor/6/60), but usually this/these will not include the AA/6/60 HA segment and usually will not include the AA/6/60 NA segment. Thus the system may encode at least one of segments NP, M, NS, PA, PB1 and/or PB2 (possibly all six) from AA/6/60.

Expression systems for influenza B viruses may encode genome segments derived from a plurality of different wild-type strains. The system may encode 1 or more (e.g. 1, 2, 3, 4, 5 or 6) genome segments from a AA/1/66 influenza virus (B/Ann Arbor/1/66), but usually this/these will not include the AA/1/66 HA segment and usually will not include the AA/1/66 NA segment. Thus the system may encode at least one of segments NP, M, NS, PA, PB1 and/or PB2 from AA/1/66.

Viral segments and sequences from the A/PR/8/34, A/AA/6/60, and B/AA/1/66 strains are widely available. Their sequences are available on the public databases e.g. GI:89779337, GI:89779334, GI:89779332, GI:89779320, GI:89779327, GI:89779325, GI:89779322, GI:89779329.

In some embodiments it may be advantageous to provide an influenza virus whose genome does not encode a NS1 viral protein, or whose NS1 protein is truncated. NS1 knockout mutants are described in reference 16. Truncations are known in the art (e.g. see references 17 & 18) and include truncations which leave only the first N-terminal 126 amino acids of NS1. These NS1-mutant virus strains are particularly suitable for preparing live attenuated influenza vaccines.

A reverse genetics system for influenza virus (and certain other viruses) may include an expression construct which leads to expression of an accessory protein in the host cell. For instance, it can be advantageous to express a non-viral serine protease (e.g. trypsin).

As mentioned above, it can be advantageous to split viral segments between several expression constructs. This is also true for influenza virus.

In one embodiment, a first non-bacterial expression construct comprises coding sequences for influenza virus A or B genome segments PB2, PB1, PA, NP and NS. A second non-bacterial construct comprises a coding sequence for influenza virus A or B genome segment HA. The NA and M genome segments are encoded either on the first construct (to give a "7:1" system) or on the second construct (to give a 5:3 system), or the M segment is on the first construct and the NA segment is on the second construct (6:2). For influenza A virus, the first construct ideally encodes segments from a PR/8/34, AA/6/60 or AA/1/66 strain. The segments encoded on the second construct can come from different strain(s) from the segments on the first construct, thereby facilitating the strain reassortment which is regularly performed prior to influenza vaccine manufacture. Each of the coding sequences for the eight viral segments has a promoter for driving its expression as a vRNA e.g. a pol-I promoter. The first construct should also comprise coding sequences for expressing at least the PB1, PB2, PA and NP viral proteins e.g. each under the control of a pol-II promoter. Usefully, to reduce the overall length of the construct (thus increasing stability), the coding sequences for at least the PB1, PB2, PA and NP segments are flanked by a pol-I promoter at one end and a pol-II promoter at the other end, such that bidirectional expression can provide the viral segments and the viral proteins from the same DNA coding sequence. Thus pol-I promoter and terminator sequences may flank the sequence encoding the viral segment, and these may be surrounded by pol-II promoter and terminator sequences. The pair of linear constructs can be transfected into animal cells which recognise the pol-I and pol-II promoters (e.g. into mammalian cells such as MDCK or PER.C6 cells) to provide infectious influenza virus.

In another embodiment, a bacterial plasmid comprises coding sequences for influenza virus A or B genome segments PB2, PB1, PA, NP and NS. A non-bacterial construct (preferably linear) comprises a coding sequence for influenza virus A or B genome segment HA. The NA and M genome segments are encoded either on the plasmid (to give a "7:1" system) or on the non-bacterial construct (to give a 5:3 system), or the M segment is on the plasmid and the NA segment is on the non-bacterial construct (6:2). For influenza A virus, the plasmid ideally encodes segments from a PR/8/34, AA/6/60 or AA/1/66 strain. The segments encoded on the non-bacterial construct can come from different strain(s) from the segments on the plasmid, thereby facilitating the strain reassortment which is regularly performed prior to influenza vaccine manufacture. Each of the coding sequences for the eight viral segments has a promoter for driving its expression as a vRNA e.g. a pol-I promoter. The plasmid should also comprise coding sequences for expressing at least the PB1, PB2, PA and NP viral proteins e.g. each under the control of a pol-II promoter. Usefully, to reduce the overall length of the plasmid, the coding sequences for at least the PB1, PB2, PA and NP segments are flanked by a pol-I promoter at one end and a pol-II promoter at the other end, such that bidirectional expression can provide the viral segments and the viral proteins from the same DNA coding sequence. Thus pol-I promoter and terminator sequences may flank the sequence encoding the viral segment, and these may be surrounded by pol-II promoter and terminator sequences. The plasmid and the non-bacterial constructs are maintained separately prior to use, but can then both be transfected into animal cells which recognise the pol-I and pol-II promoters (e.g. into mammalian cells such as MDCK or PER.C6 cells) to provide infectious influenza virus.

In another embodiment, a non-bacterial construct (preferably linear) comprises coding sequences for influenza virus A or B genome segments PB2, PB1, PA, NP and NS. A bacterial plasmid comprises a coding sequence for influenza virus A or B genome segment HA. The NA and M genome segments are encoded: on the non-bacterial construct (to give a "7:1" system); or on the plasmid (to give a 5:3 system); or on separate plasmids (to give a 5:1:1:1 system); or the NA segment is on the same plasmid as HA while the M segment is on the non-bacterial construct (6:2); or the NA segment is on a second plasmid and the M segment is on the non-bacterial construct (6:1:1). For influenza A virus, the non-bacterial construct ideally encodes segments from a PR/8/34, AA/6/60 or AA/1/66 strain. The segments encoded on the plasmid can come from different strain(s) from the segments on the non-bacterial construct, thereby facilitating the strain reassortment which is regularly performed prior to influenza vaccine manufacture. Each of the coding sequences for the eight viral segments has a promoter for driving its expression as a vRNA e.g. a pol-I promoter. The non-bacterial construct should also comprise coding sequences for expressing at least the PB1, PB2, PA and NP viral proteins e.g. each under the control of a pol-II promoter. Usefully, to reduce the overall length of the non-bacterial construct, the coding sequences for at least the PB1, PB2, PA and NP segments are flanked by a pol-I promoter at one end and a pol-II promoter at the other end, such that bidirectional expression can provide the viral segments and the viral proteins from the same DNA coding sequence. Thus pol-I promoter and terminator sequences may flank the sequence encoding the viral segment, and these may be surrounded by pol-II promoter and terminator sequences. The plasmid and the non-bacterial constructs are maintained separately prior to use, but can then both be transfected into animal cells which recognise the pol-I and pol-II promoters (e.g. into mammalian cells such as MDCK or PER.C6 cells) to provide infectious influenza virus.

In some embodiments, however, a single construct is used to encode the complete viral genome. Thus the invention provides a non-bacterial expression construct comprising coding sequences for expressing all eight influenza virus A or B genome segments. This construct is ideally a linear construct e.g. between 22-26 kbp. Each of the coding sequences for the eight viral segments has a promoter for driving its expression as a vRNA e.g. a pol-I promoter. The construct should also comprise coding sequences for expressing at least the PB1, PB2, PA and NP viral proteins e.g. each under the control of a pol-II promoter. Usefully, to reduce the overall length of the construct, the coding sequences for the PB1, PB2, PA and NP segments (and preferably for all eight viral segments) are flanked by a pol-I promoter at one end and a pol-II promoter at the other end, such that bidirectional expression can provide the viral segments and the viral proteins from the same DNA coding sequence. Thus pol-I promoter and terminator sequences may flank the sequence encoding the viral segment, and these may be surrounded by pol-II promoter and terminator sequences. This linear construct can be transfected into animal cells which recognise the pol-I and pol-II promoters (e.g. into mammalian cells such as MDCK or PER.C6 cells) to provide infectious influenza virus.

Cells

The present invention can be performed in any cell that can express the virus of interest after transfection with the expression construct(s). The invention will typically use a cell line, although primary cells may be used as an alternative. The cell will typically be mammalian, although avian or insect cells can also be used. Suitable mammalian cells include, but are not limited to, hamster, cattle, primate (including humans and monkeys) and dog cells. Various cell types may be used, such as kidney cells, fibroblasts, retinal cells, lung cells, etc. Examples of suitable hamster cells are the cell lines having the names BHK21 or HKCC. Suitable monkey cells are e.g. African green monkey cells, such as kidney cells as in the Vero cell line [19-21]. Suitable dog cells are e.g. kidney cells, as in the CLDK and MDCK cell lines. Suitable avian cells include the EBx cell line derived from chicken embryonic stem cells, EB45, EB14, and EB14-074 [22].

Further suitable cells include, but are not limited to: CHO; 293T; MRC 5; PER.C6 [23]; FRhL2; W1-38; etc. Suitable cells are widely available e.g. from the American Type Cell Culture (ATCC) collection [24], from the Coriell Cell Repositories [25], or from the European Collection of Cell Cultures (ECACC). For example, the ATCC supplies various different Vero cells under catalogue numbers CCL 81, CCL 81.2, CRL 1586 and CRL-1587, and it supplies MDCK cells under catalogue number CCL 34. PER.C6 is available from the ECACC under deposit number 96022940.

Preferred cells (particularly for growing influenza viruses) for use in the invention are MDCK cells [26-28], derived from Madin Darby canine kidney. The original MDCK cells are available from the ATCC as CCL 34. It is preferred that derivatives of these or other MDCK cells are used. Such derivatives were described, for instance, in reference 26 which discloses MDCK cells that were adapted for growth in suspension culture ('MDCK 33016' or '33016-PF', deposited as DSM ACC 2219). Furthermore, reference 29 discloses MDCK-derived cells that grow in suspension in serum free culture ('B-702', deposited as FERM BP-7449). In some embodiments, the MDCK cell line used may be tumorigenic, but it is also envisioned to use non-tumorigenic MDCK cells. For example, reference 30 discloses non-tumorigenic MDCK cells, including 'MDCK-S' (ATCC PTA-6500), 'MDCK-SF101' (ATCC PTA-6501), 'MDCK-SF102' (ATCC PTA-6502) and 'MDCK-SF103' (ATCC PTA-6503). Reference 31 discloses MDCK cells with high susceptibility to infection, including 'MDCK.5F1' cells (ATCC CRL 12042).

It is possible to use a mixture of more than one cell type for viral rescue, but it is preferred to use a single cell type e.g. using monoclonal cells. Preferably, the cells are from a single cell line. The same cell line may be used downstream for subsequent propagation of the virus e.g. during virus growth.

Preferably, the cells are cultured in the absence of serum, to avoid a common source of contaminants. Various serum-free media for eukaryotic cell culture are known to the person skilled in the art e.g. Iscove's medium, ultra CHO medium (BioWhittaker), EX-CELL (JRH Biosciences). Furthermore, protein-free media may be used e.g. PF-CHO (JRH Biosciences). Otherwise, the cells for replication can also be cultured in the customary serum-containing media (e.g. MEM or DMEM medium with 0.5% to 10% of fetal calf serum).

The cells may be in adherent culture or in suspension.

Vaccines

The invention provides an influenza virus produced by a host cell of the invention. This influenza virus may be used in various ways e.g. as a seed virus for vaccine manufacture.

Thus the invention can utilise a rescued virus to produce vaccines.

Vaccines (particularly for influenza virus) are generally based either on live virus or on inactivated virus e.g. see chapters 17 & 18 of reference 32. Inactivated vaccines may be based on whole virions, 'split' virions, or on purified surface antigens. Antigens can also be presented in the form of virosomes. The invention can be used for manufacturing any of these types of vaccine.

Where an inactivated virus is used, the vaccine may comprise whole virion, split virion, or purified surface antigens (for influenza, including hemagglutinin and, usually, also including neuraminidase). Chemical means for inactivating a virus include treatment with an effective amount of one or more of the following agents: detergents, formaldehyde, β-propiolactone, methylene blue, psoralen, carboxyfullerene (C60), binary ethylamine, acetyl ethyleneimine, or combinations thereof. Non-chemical methods of viral inactivation are known in the art, such as for example UV light or gamma irradiation.

Virions can be harvested from virus-containing fluids, e.g. allantoic fluid or cell culture supernatant, by various methods. For example, a purification process may involve zonal centrifugation using a linear sucrose gradient solution that includes detergent to disrupt the virions. Antigens may then be purified, after optional dilution, by diafiltration.

Split virions are obtained by treating purified virions with detergents (e.g. ethyl ether, polysorbate 80, deoxycholate, tri-N-butyl phosphate, Triton X-100, Triton N101, cetyltrimethylammonium bromide, Tergitol NP9, etc.) to produce subvirion preparations, including the 'Tween-ether' splitting process. Methods of splitting influenza viruses, for example are well known in the art e.g. see refs. 33-38, etc. Splitting of the virus is typically carried out by disrupting or fragmenting whole virus, whether infectious or non-infectious with a disrupting concentration of a splitting agent. The disruption results in a full or partial solubilisation of the virus proteins, altering the integrity of the virus. Preferred splitting agents are non-ionic and ionic (e.g. cationic) surfactants e.g. alkylglycosides, alkylthioglycosides, acyl sugars, sulphobetaines, betains, polyoxyethylenealkylethers, N,N-dialkyl-Glucamides, Hecameg, alkylphenoxy-polyethoxyethanols, NP9, quaternary ammonium compounds, sarcosyl, CTABs (cetyl trimethyl ammonium bromides), tri-N-butyl phosphate, Cetavlon, myristyltrimethylammonium salts, lipofectin, lipofectamine, and DOT-MA, the octyl- or nonylphenoxy polyoxyethanols (e.g. the Triton surfactants, such as Triton X-100 or Triton N101), polyoxyethylene sorbitan esters (the Tween surfactants), polyoxyethylene ethers, polyoxyethlene esters, etc. One useful splitting procedure uses the consecutive effects of sodium deoxycholate and formaldehyde, and splitting can take place during initial virion purification (e.g. in a sucrose density gradient solution). Thus a splitting process can involve clarification of the virion-containing material (to remove non-virion material), concentration of the harvested virions (e.g. using an adsorption method, such as $CaHPO_4$ adsorption), separation of whole virions from non-virion material, splitting of virions using a splitting agent in a density gradient centrifugation step (e.g. using a sucrose gradient that contains a splitting agent such as sodium deoxycholate), and then filtration (e.g. ultrafiltration) to remove undesired materials. Split virions can usefully be resuspended in sodium phosphate-buffered isotonic sodium chloride solution.

Purified influenza virus surface antigen vaccines comprise the surface antigens hemagglutinin and, typically, also neuraminidase. Processes for preparing these proteins in purified form are well known in the art. The FLUVIRIN™, AGRIPPAL™ and INFLUVAC™ products are influenza subunit vaccines.

Another form of inactivated antigen is the virosome [39] (nucleic acid free viral-like liposomal particles). Virosomes can be prepared by solubilization of virus with a detergent followed by removal of the nucleocapsid and reconstitution of the membrane containing the viral glycoproteins. An alternative method for preparing virosomes involves adding viral membrane glycoproteins to excess amounts of phospholipids, to give liposomes with viral proteins in their membrane.

The invention may also be used to produce live vaccines. Such vaccines are usually prepared by purifying virions from virion-containing fluids. For example, the fluids may be clarified by centrifugation, and stabilized with buffer (e.g. containing sucrose, potassium phosphate, and monosodium glutamate).

The virus may be attenuated. The virus may be temperature-sensitive. The virus may be cold-adapted. These three features are particularly useful when using live virus as an antigen, and reverse genetics is particularly useful for preparing such strains.

HA is the main immunogen in inactivated influenza vaccines, and vaccine doses are standardised by reference to HA levels, typically measured by SRID. Existing vaccines typically contain about 15 μg of HA per strain, although lower doses can be used e.g. for children, or in pandemic situations, or when using an adjuvant. Fractional doses such as ½ (i.e. 7.5 μg HA per strain), ¼ and ⅛ have been used, as have higher doses (e.g. 3× or 9× doses [40,41]). Thus vaccines may include between 0.1 and 150 μg of HA, per influenza strain, preferably between 0.1 and 50 μg e.g. 0.1-20 μg, 0.1-15 μg, 0.1-10 μg, 0.5-5 μg, etc. Particular doses include e.g. about 45, about 30, about 15, about 10, about 7.5, about 5, about 3.75, about 1.9, about 1.5, etc. per strain.

For live vaccines, dosing is measured by median tissue culture infectious dose ($TCID_{50}$) rather than HA content, and a $TCID_{50}$ of between $10^6$ and $10^8$ (preferably between $10^{6.5}$-$10^{7.5}$) per strain is typical.

Influenza strains used with the invention may have a natural HA as found in a wild-type virus, or a modified HA. For instance, it is known to modify HA to remove determinants (e.g. hyper-basic regions around the HA1/HA2 cleavage site) that cause a virus to be highly pathogenic in avian species. The use of reverse genetics facilitates such modifications.

Influenza virus strains for use in vaccines change from season to season. In inter-pandemic periods, vaccines typically include two influenza A strains (H1N1 and H3N2) and one influenza B strain, and trivalent vaccines are typical. The invention may also use pandemic viral strains (i.e. strains to which the vaccine recipient and the general human population are immunologically naïve, in particular of influenza A virus), such as H2, H5, H7 or H9 subtype strains, and influenza vaccines for pandemic strains may be monovalent or may be based on a normal trivalent vaccine supplemented by a pandemic strain. Depending on the season and on the nature of the antigen included in the vaccine, however, the invention may protect against one or more of HA subtypes H1, H2, H3, H4, H5, H6, H7, H8, H9, H10, H11, H12, H13, H14, H15 or H16. The invention may protect against one or more of influenza A virus NA subtypes N1, N2, N3, N4, N5, N6, N7, N8 or N9.

As well as being suitable for immunizing against inter-pandemic strains, the compositions of the invention are particularly useful for immunizing against pandemic or potentially-pandemic strains. The characteristics of an influenza strain that give it the potential to cause a pandemic outbreak are: (a) it contains a new hemagglutinin compared to the hemagglutinins in currently-circulating human strains, i.e. one that has not been evident in the human population for over a decade (e.g. H2), or has not previously been seen at all in the human population (e.g. H5, H6 or 1-19, that have generally been found only in bird populations), such that the human population will be immunologically naïve to the strain's hemagglutinin; (b) it is capable of being transmitted horizontally in the human population; and (c) it is pathogenic to humans. A virus with H5 hemagglutinin type is preferred for immunizing against pandemic influenza, such as a H5N1 strain. Other possible strains include H5N3, H9N2, H2N2, H7N1 and H7N7, and any other emerging potentially pandemic strains. The invention is particularly suitable for protecting against potential pandemic virus strains that can or have spread from a non-human animal population to humans, for example a swine-origin H1N1 influenza strain. The invention is then suitable for vaccinating humans as well as non-human animals.

Other strains whose antigens can usefully be included in the compositions are strains which are resistant to antiviral therapy (e.g. resistant to oseltamivir [42] and/or zanamivir), including resistant pandemic strains [43].

Compositions of the invention may include antigen(s) from one or more (e.g. 1, 2, 3, 4 or more) influenza virus strains, including influenza A virus and/or influenza B virus. Where a vaccine includes more than one strain of influenza, the different strains are typically grown separately and are mixed after the viruses have been harvested and antigens have been prepared. Thus a process of the invention may include the step of mixing antigens from more than one influenza strain. A trivalent vaccine is typical, including antigens from two influenza A virus strains and one influenza B virus strain. A tetravalent vaccine is also useful [44], including antigens from two influenza A virus strains and two influenza B virus strains, or three influenza A virus strains and one influenza B virus strain.

Viruses for preparation of influenza vaccines may be grown in eggs or in cell culture. The current standard method for influenza virus growth for vaccines uses embryonated SPF hen eggs, with virus being purified from the egg contents (allantoic fluid). Cell culture is used to make the OPTAFLU™ product. Cells are preferably cultured in serum-free or protein-free media for growing virus used for vaccine production. Culturing of cells preferably occurs at a temperature between 30 and 40° C. Cells may be cultured during viral growth at a temperature of between 30-36° C. or between 32-34° C. or at 33° C. Incubation of infected cells in this temperature range results in production of an improved influenza virus for vaccine use [45]. Virus may be grown on cells in adherent culture or in suspension. Microcarrier cultures can be used. In some embodiments, the cells may thus be adapted for growth in suspension. Growth in cell culture may use the same cell type as was used for the reverse genetics which gave rise to the virus.

A method may include a post-growth step of harvesting and isolation of viruses or their antigens from culture fluids. During isolation of viruses or proteins, the cells are separated from the culture medium by standard methods like separation, filtration or ultrafiltration. The viruses or their antigens are then concentrated according to methods sufficiently known to those skilled in the art, like gradient centrifugation, filtration, precipitation, chromatography, etc., and then purified. It is also preferred according to the invention that the viruses are inactivated during or after purification. Virus inactivation can occur, for example, by β-propiolactone or formaldehyde at any point within the purification process.

Host Cell DNA

Where virus has been isolated and/or grown on a cell line, it is standard practice to minimize the amount of residual cell line DNA in the final vaccine, in order to minimize any oncogenic activity of the DNA. Thus a vaccine composition prepared according to the invention preferably contains less than 10 ng (preferably less than 1 ng, and more preferably less than 100 pg) of residual host cell DNA per dose, although trace amounts of host cell DNA may be present.

It is preferred that the average length of any residual host cell DNA is less than 500 bp e.g. less than 400 bp, less than 300 bp, less than 200 bp, less than 100 bp, etc.

Contaminating DNA can be removed during vaccine preparation using standard purification procedures e.g. chromatography, etc. Removal of residual host cell DNA can be enhanced by nuclease treatment e.g. by using a DNase. A convenient method for reducing host cell DNA contamination is disclosed in references 46 & 47, involving a two-step treatment, first using a DNase (e.g. Benzonase), which may be used during viral growth, and then a cationic detergent (e.g. CTAB), which may be used during virion disruption. Treatment with an alkylating agent, such as β-propiolactone, can also be used to remove host cell DNA, and advantageously may also be used to inactivate virions [48].

Pharmaceutical Compositions

Vaccine compositions manufactured according to the invention are pharmaceutically acceptable. They usually include components in addition to the antigens e.g. they typically include one or more pharmaceutical carrier(s) and/or excipient(s). As described below, adjuvants may also be included. A thorough discussion of such components is available in reference 49.

Vaccine compositions will generally be in aqueous form. However, some vaccines may be in dry form, e.g. in the form of injectable solids or dried or polymerized preparations on a patch.

Vaccine compositions may include preservatives such as thiomersal. It is preferred, however, that the vaccine should be substantially free from (i.e. less than 5 μg/ml) mercurial material e.g. thiomersal-free [37,50]. Vaccines containing no mercury are more preferred. α-tocopherol succinate can be included as an alternative to mercurial compounds [37]. Preservative-free vaccines are useful.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Vaccine compositions will generally have an osmolality of between 200 mOsm/kg and 400 mOsm/kg, preferably between 240-360 mOsm/kg, and will more preferably fall within the range of 290-310 mOsm/kg. Osmolality has previously been reported not to have an impact on pain caused by vaccination [51], but keeping osmolality in this range is nevertheless preferred.

Vaccine compositions may include one or more buffers. The pH of a vaccine composition will generally be between 5.0 and 8.1, and more typically between 6.0 and 8.0 e.g. 6.5 and 7.5, or between 7.0 and 7.8.

The vaccine composition is preferably sterile. The vaccine composition is preferably non-pyrogenic e.g. containing <1 EU (endotoxin unit, a standard measure) per dose, and preferably <0.1 EU per dose. The vaccine composition is preferably gluten-free.

Vaccine compositions of the invention may include detergent e.g. a polyoxyethylene sorbitan ester surfactant (known as 'Tweens'), an octoxynol (such as octoxynol-9 (Triton X-100) or t-octylphenoxypolyethoxyethanol), a cetyl trimethyl ammonium bromide ('CTAB'), or sodium deoxycholate, particularly for a split or surface antigen vaccine. The detergent may be present only at trace amounts. Thus the vaccine may include less than 1 mg/ml of each of octoxynol-10 and polysorbate 80. Other residual components in trace amounts could be antibiotics (e.g. neomycin, kanamycin, polymyxin B).

A vaccine composition may include material for a single immunisation, or may include material for multiple immunisations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

Influenza vaccines are typically administered in a dosage volume of about 0.5 ml, although a half dose (i.e. about 0.25 ml) may be administered to children.

Suitable containers for compositions of the invention (or kit components) include vials, syringes (e.g. disposable pre-filled syringes), nasal sprays, etc. These containers should be sterile. A vial may include a single dose of vaccine, or it may include more than one dose (a 'multidose' vial) e.g. 10 doses. Preferred vials are made of colourless glass. A vial may have a cap that permits aseptic removal of its contents, particularly for multidose vials. Containers may be marked to show a half-dose volume e.g. to facilitate delivery to children. For instance, a syringe containing a 0.5 ml dose may have a mark showing a 0.25 ml volume.

Where a glass container (e.g. a syringe or a vial) is used, then it is preferred to use a container made from a borosilicate glass rather than from a soda lime glass.

Where a component is packaged into a syringe, the syringe may have a needle attached to it. If a needle is not attached, a separate needle may be supplied with the syringe for assembly and use. Such a needle may be sheathed. Safety needles are preferred. 1-inch 23-gauge, 1-inch 25-gauge and ⅝-inch 25-gauge needles are typical.

Adjuvants

Vaccine compositions of the invention may advantageously include an adjuvant, which can function to enhance the immune responses (humoral and/or cellular) elicited in a subject who receives the composition. Preferred adjuvants comprise oil-in-water emulsions. Various such adjuvants are known, and they typically include at least one oil and at least one surfactant, with the oil(s) and surfactant(s) being biodegradable (metabolisable) and biocompatible. The oil droplets in the emulsion are generally less than 5 μm in diameter, and ideally have a sub-micron diameter, with these small sizes being achieved with a microfluidiser to provide stable emulsions. Droplets with a size less than 220 nm are preferred as they can be subjected to filter sterilization.

Specific oil-in-water emulsion adjuvants useful with the invention include, but are not limited to:

A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' [52-54], as described in more detail in Chapter 10 of ref. 55 and chapter 12 of ref. 56. The MF59 emulsion advantageously includes citrate ions e.g. 10 mM sodium citrate buffer.

An emulsion of squalene, DL-α-tocopherol, and polysorbate 80 (Tween 80). The emulsion may include phosphate buffered saline. It may also include Span 85 (e.g. at 1%) and/or lecithin. These emulsions may have from 2 to 10% squalene, from 2 to 10% tocopherol and from 0.3 to 3% Tween 80, and the weight ratio of squalene:tocopherol is preferably ≤1 as this provides a more stable emulsion. Squalene and Tween 80 may be present volume ratio of about 5:2 or at a weight ratio of about 11:5. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm. The emulsion may also include a 3-de-O-acylated monophosphoryl lipid A (3d-MPL). Another useful emulsion of this type may comprise, per human dose, 0.5-10 mg squalene, 0.5-11 mg tocopherol, and 0.1-4 mg polysorbate 80 [57].

An emulsion of squalene, a tocopherol, and a Triton detergent (e.g. Triton X-100). The emulsion may also include a 3d-MPL (see below). The emulsion may contain a phosphate buffer.

An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 μg/ml polysorbate 80, 110 μg/ml Triton X-100 and 100 μg/ml α-tocopherol succinate), and these concentrations should include any contribution of these components from antigens. The emulsion may also include squalene. The emulsion may also include a 3d-MPL (see below). The aqueous phase may contain a phosphate buffer.

An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant [58] (0.05-1% Thr-MDP, 5% squalane, 2.5% Pluronic L121 and 0.2% polysorbate 80). It can also be used without the Thr-MDP, as in the "AF" adjuvant [59] (5% squalane, 1.25% Pluronic L121 and 0.2% polysorbate 80). Microfluidisation is preferred.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm [60]. The emulsion may also include one or more of: alditol; a cryoprotective agent (e.g. a sugar, such as dodecylmaltoside and/or sucrose); and/or an alkylpolyglycoside. The emulsion may include a TLR4 agonist [61]. Such emulsions may be lyophilized.

An emulsion of squalene, poloxamer 105 and Abil-Care [62]. The final concentration (weight) of these components in adjuvanted vaccines are 5% squalene, 4% poloxamer 105 (pluronic polyol) and 2% Abil-Care 85 (Bis-PEG/PPG-16/16 PEG/PPG-16/16 dimethicone; caprylic/capric triglyceride).

An emulsion having from 0.5-50% of an oil, 0.1-10% of a phospholipid, and 0.05-5% of a non-ionic surfactant. As described in reference 63, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

An emulsion in which a saponin (e.g. QuilA or QS21) and a sterol (e.g. a cholesterol) are associated as helical micelles [64].

In some embodiments an emulsion may be mixed with antigen extemporaneously, at the time of delivery, and thus the adjuvant and antigen may be kept separately in a packaged or distributed vaccine, ready for final formulation at the time of use. In other embodiments an emulsion is mixed with antigen during manufacture, and thus the composition is packaged in a liquid adjuvanted form.

Methods of Treatment, and Administration of the Vaccine

The invention provides a vaccine manufactured according to the invention. These vaccine compositions are suitable for administration to human or non-human animal subjects, such as pigs, and the invention provides a method of raising an immune response in a subject, comprising the step of administering a composition of the invention to the subject. The invention also provides a composition of the invention for use as a medicament, and provides the use of a composition of the invention for the manufacture of a medicament for raising an immune response in a subject.

The immune response raised by these methods and uses will generally include an antibody response, preferably a protective antibody response.

Compositions of the invention can be administered in various ways. The most preferred immunisation route is by intramuscular injection (e.g. into the arm or leg), but other available routes include subcutaneous injection or intranasal [65-67].

Vaccines prepared according to the invention may be used to treat both children and adults.

Treatment can be by a single dose schedule or a multiple dose schedule. Multiple doses may be used in a primary immunisation schedule and/or in a booster immunisation schedule. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

Vaccines produced by the invention may be administered to patients at substantially the same time as (e.g. during the same medical consultation or visit to a healthcare professional or vaccination centre) other vaccines.

Similarly, vaccines of the invention may be administered to patients at substantially the same time as (e.g. during the same medical consultation or visit to a healthcare professional) an antiviral compound, and in particular an antiviral compound active against influenza virus (e.g. oseltamivir and/or zanamivir).

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encephalopathies (TSEs), and in particular free from bovine spongiform encephalopathy (BSE). Overall, it is preferred to culture cells in the total absence of animal-derived materials.

MODES FOR CARRYING OUT THE INVENTION

Source influenza viruses are S-OIV strain A/California/4/09 for HA and NA segments and PR/8/34 for the remaining six backbone segments. DNA sequences encoding these eight segments are prepared, with each segment being flanked by a human pol-I promoter at one end and a pol-I terminator at the other end. These pol-I elements are surrounded by a pol-II promoter from CMV and a pol-II terminator sequence and polA signal. The pol-I promoter drives transcription of a negative sense viral RNA segment with faithful wild-type vRNA termini. The pol-II promoter drives transcription of a mRNA encoding the viral protein. DNA segments for each segment are joined to give a single linear DNA molecule, ~24 kbp, encoding the whole reassortant influenza virus genome. The overall synthesis of this molecule follows the general methods disclosed by Gibson et al. in reference 8.

The linear DNA construct is transfected into a culture of MDCK 33016 cells. This cell line has been found to recognise the human pol-I promoter for influenza virus reverse genetics rescue. Incubation of the transfected cells soon leads to the appearance of reassortant influenza virus in the culture medium. This strain ("RG-lin-CA-1") can be purified by conventional methods and used as a seed for vaccine manufacture.

It will be understood that the invention has been described by way of example only and modifications may be made whilst remaining within the scope and spirit of the invention.

REFERENCES

[1] Racaniello & Baltimore (1981) *Science* 214:916-919.
[2] Kaplan et al. (1985) *Proc Natl Acad Sci USA* 82: 8424-8428.
[3] Fodor et al. (1999) *J. Virol* 73(11):9679-9682.
[4] Hoffmann et al. (2002) *Proc Natl Acad Sci USA* 99:11411-6.
[5] Kobayashi et al. (2007) *Cell Host Microbe* 19; 1(2):147-57.
[6] WO2009/000891.
[7] Kodumal et al. (2004) *Proc Natl Acad Sci USA*. 101 (44):15573-8.
[8] Gibson et al. (2008) *Science* 319(5867):1215-20.
[9] Yount et al. (2002) *J Virol* 76:11065-78.
[10] Wang & Kushner (1991) *Gene* 100:195-9.
[11] Shi & Biek (1995) *Gene* 164:55-8.
[12] WO2006/067211.
[13] WO01/83794.
[14] WO2007/002008.
[15] WO2007/124327.
[16] U.S. Pat. No. 6,468,544.
[17] WO99/64068.
[18] Efferson et al. (2006) *J Virol.* 80(1):383-94.
[19] Kistner et al. (1998) *Vaccine* 16:960-8.
[20] Kistner et al. (1999) *Dev Biol Stand* 98:101-110.
[21] Bruhl et al. (2000) *Vaccine* 19:1149-58.
[22] WO2006/108846.
[23] Pau et al. (2001) *Vaccine* 19:2716-21.

[24] http://www.atcc.org/
[25] http://locus.umdnj.edu/
[26] WO97/37000.
[27] Brands et al. (1999) *Dev Biol Stand* 98:93-100.
[28] Halperin et al. (2002) *Vaccine* 20:1240-7.
[29] EP-A-1260581 (WO01/64846).
[30] WO2006/071563.
[31] WO2005/113758.
[32] Vaccines. (eds. Plotkins & Orenstein). 4th edition, 2004, ISBN: 0-7216-9688-0.
[33] WO02/28422.
[34] WO02/067983.
[35] WO02/074336.
[36] WO01/21151.
[37] WO02/097072.
[38] WO2005/113756.
[39] Huckriede et al. (2003) *Methods Enzymol* 373:74-91.
[40] Treanor et al. (1996) *J Infect Dis* 173:1467-70.
[41] Keitel et al. (1996) *Clin Diagn Lab Immunol* 3:507-10.
[42] Herlocher et al. (2004) *J Infect Dis* 190(9):1627-30.
[43] Le et al. (2005) *Nature* 437(7062):1108.
[44] WO2008/068631.
[45] WO97/37001.
[46] EP-B-0870508.
[47] U.S. Pat. No. 5,948,410.
[48] WO2007/052163.
[49] Gennaro (2000) *Remington: The Science and Practice of Pharmacy*. 20th ed, ISBN: 0683306472.
[50] Banzhoff (2000) *Immunology Letters* 71:91-96.
[51] Nony et al. (2001) *Vaccine* 27:3645-51.
[52] WO90/14837.
[53] Podda & Del Giudice (2003) *Expert Rev Vaccines* 2:197-203.
[54] Podda (2001) *Vaccine* 19: 2673-2680.
[55] *Vaccine Design: The Subunit and Adjuvant Approach* (eds. Powell & Newman) Plenum Press 1995 (ISBN 0-306-44867-X).
[56] *Vaccine Adjuvants: Preparation Methods and Research Protocols* (Volume 42 of *Methods in Molecular Medicine* series). ISBN: 1-59259-083-7. Ed. O'Hagan.
[57] WO2008/043774.
[58] Allison & Byars (1992) *Res Immunol* 143:519-25.
[59] Hariharan et al. (1995) *Cancer Res* 55:3486-9.
[60] US-2007/0014805.
[61] US-2007/0191314.
[62] Suli et al. (2004) *Vaccine* 22(25-26):3464-9.
[63] WO95/11700.
[64] WO2005/097181.
[65] Greenbaum et al. (2004) *Vaccine* 22:2566-77.
[66] Zurbriggen et al. (2003) *Expert Rev Vaccines* 2:295-304.
[67] Piascik (2003) *J Am Pharm Assoc* (Wash D.C.). 43:728-30.

The invention claimed is:

1. A eukaryotic host cell comprising at least one plasmid bacterial expression construct and at least one non-bacterial expression construct, wherein each construct comprises coding sequences for at least one genome segment of a segmented RNA virus.

2. The eukaryotic host cell of claim 1, wherein the segmented RNA virus is an influenza virus.

3. The eukaryotic host cell of claim 1, wherein the RNA virus genome segments from the at least one plasmid bacterial expression construct and the at least one non-bacterial expression construct are different.

4. The eukaryotic host cell of claim 1, wherein the at least one non-bacterial expression construct is linear.

5. The eukaryotic host cell of claim 1, wherein the at least one non-bacterial expression construct is circular.

6. The eukaryotic host cell of claim 1, wherein the at least one plasmid bacterial expression construct and the at least one non-bacterial expression construct encode for both viral protein and viral RNA expression.

7. The eukaryotic host cell of claim 6, wherein the at least one plasmid bacterial expression construct and the at least one non-bacterial expression construct each comprise a bi-directional expression construct.

8. A method of preparing a eukaryotic host cell, comprising inserting at least one plasmid bacterial expression construct and at least one non-bacterial expression construct into the eukaryotic host cell, wherein each construct comprises coding sequences for at least one genome segment of a segmented RNA virus.

9. The method of claim 8, wherein the at least one plasmid bacterial expression construct and the at least one non-bacterial expression construct encode for both viral protein and viral RNA expression.

10. The method of claim 9, wherein the at least one plasmid bacterial expression construct and the at least one non-bacterial expression construct each comprise a bi-directional expression construct.

11. The method of claim 8, wherein the segmented RNA virus is an influenza virus.

12. The method of claim 8, wherein the RNA virus genome segments from the at least one plasmid bacterial expression construct and the at least one non-bacterial expression construct are different.

13. The method of claim 8, wherein the at least one non-bacterial expression construct is linear.

14. The method of claim 8, wherein the at least one non-bacterial expression construct is circular.

15. A method of preparing a viral vaccine, comprising:
infecting an egg with a segmented RNA virus produced by culturing the egg under conditions that enable expression of segments of the RNA virus from a reverse genetics system comprising at least one plasmid bacterial expression construct and at least one non-bacterial expression construct, wherein each construct comprises coding sequences for at least one genome segment of the segmented RNA virus;

growing the segmented RNA virus in the infected egg; and preparing a vaccine from the grown virus.

16. The method of claim 15, wherein the segmented RNA virus is an influenza virus.

17. The method of claim 15, wherein the RNA virus genome segments from the at least one plasmid bacterial expression construct and the at least one non-bacterial expression construct are different.

18. The method of claim 15, wherein the at least one non-bacterial expression construct is linear.

19. The method of claim 15, wherein the at least one non-bacterial expression construct is circular.

20. The method of claim 15, wherein the at least one plasmid bacterial expression construct and the at least one non-bacterial expression construct encode for both viral protein and viral RNA expression.

21. The method of claim 20, wherein the at least one plasmid bacterial expression construct and the at least one non-bacterial expression construct each comprise a bi-directional expression construct.

* * * * *